(12) United States Patent
Suau et al.

(10) Patent No.: US 8,802,067 B2
(45) Date of Patent: *Aug. 12, 2014

(54) COMB POLYMERS FOR THE HAIR

(71) Applicant: Coatex, Genay (FR)

(72) Inventors: Jean-Marc Suau, Lucenay (FR); Olivier Guerret, Pern (FR)

(73) Assignee: Coatex S.A.S., Genay (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/147,702

(22) Filed: Jan. 6, 2014

(65) Prior Publication Data

US 2014/0120049 A1    May 1, 2014

Related U.S. Application Data

(63) Continuation of application No. 13/415,001, filed on Mar. 8, 2012, now Pat. No. 8,658,144.

(60) Provisional application No. 61/468,641, filed on Mar. 29, 2011.

(30) Foreign Application Priority Data

Mar. 28, 2011    (FR) ...................................... 11 52530

(51) Int. Cl.
| | | |
|---|---|---|
| *A61Q 5/06* | (2006.01) | |
| *A61Q 5/12* | (2006.01) | |
| *A61K 8/86* | (2006.01) | |
| *A61K 8/90* | (2006.01) | |
| *A61K 8/91* | (2006.01) | |

(52) U.S. Cl.
USPC ..................... 424/70.11; 424/70.16

(58) Field of Classification Search
CPC ............. A61K 8/91; A61Q 5/00; A61Q 5/02; A61Q 5/06

See application file for complete search history.

(56) References Cited

U.S. PATENT DOCUMENTS

| 6,231,844 B1 | 5/2001 | Nambu |
|---|---|---|
| 2006/0018863 A1 | 1/2006 | Mougin et al. |
| 2007/0082979 A1 | 4/2007 | Villard et al. |
| 2008/0311066 A1 | 12/2008 | Samain et al. |
| 2010/0273923 A1 | 10/2010 | Suau et al. |

FOREIGN PATENT DOCUMENTS

| FR | 2 861 399 A1 | 4/2005 |
|---|---|---|
| FR | 2 873 122 A1 | 1/2006 |
| FR | 2 926 558 A1 | 7/2009 |
| JP | 7-285831 A | 10/1995 |
| JP | 2000-302649 | 10/2000 |
| JP | 2003-55164 A | 2/2003 |

OTHER PUBLICATIONS

STN Accession No. 2000:765369 CAPLUS (Nov. 1, 2000).
STN Accession No. 1999-619084 CAPLUS (1989).

*Primary Examiner* — Daniel Sullivan
*Assistant Examiner* — Peter Anthopolos
(74) *Attorney, Agent, or Firm* — Oblon, Spivak, McClelland, Maier & Neustadt, L.L.P.

(57) ABSTRACT

Utilisation of (meth)acrylic comb copolymers with side chains of the hydroxy and alkoxy polyalkylene glycol type in which are present both ethylene oxide and propylene oxide links. These copolymers give a styling effect and an elimination of rinsing. The invention also relates to a cosmetic formulation containing such structures as well as a hair treatment process based on this formulation.

13 Claims, No Drawings

COMB POLYMERS FOR THE HAIR

Reference to Prior Applications

This application is a continuation application of U.S. application Ser. No. 13/415,001, filed Mar. 8, 2012, now allowed; and claims priority to U.S. provisional application Ser. No. 61/468,641, filed Mar. 29, 2011; and to French patent application 11 52530, filed Mar. 28, 2011, all incorporated herein by reference.

FIELD OF THE INVENTION

The present invention concerns the sector of additives used in cosmetic formulations intended to be applied to the scalp. It includes the utilization of (meth)acrylic comb copolymers with side chains of the hydroxy and alkoxy polyalkylene glycol type in which are present both ethylene oxide and propylene. These copolymers give the shampoos in which they are incorporated a styling effect and an elimination of rinsing that is more pronounced than that of comb copolymers manufactured from (meth)acrylic acid and side groups of the hydroxy or methoxy polyethylene glycol (MPEG) type.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. In this regard, the description herein is to be understood as illustrative in nature, and not as restrictive.

BACKGROUND OF THE INVENTION

In the field of hair care, compositions based on anionic, non-ionic and amphoteric surfactants are commonly used. They are applied to wet hair and foam is generated by massage or friction with the hands which allows, after rinsing with water, elimination of the dirt initially present.

If these formulations have good washing power, their intrinsic cosmetic properties however remain limited, particularly because of the relatively aggressive nature of the treatment to which they subject the hair: it can cause more or less marked damage to the capillary fibre, including the gradual elimination of lipids and proteins contained in the hair.

It is also necessary to use additives whose function is to improve the cosmetic properties of the hair formulations in which they are incorporated. Among these properties, "the styling effect" is one that is sought in particular: It occurs through an ease of styling and maintenance of the hair after rinsing, and by a contribution to the volume and lightness at the dry hair level.

To do this, for a long time, use has been made of cationic polymers which, because of their strong affinity for capillary fibre which is anionic in nature, will have a persistent effect on the hair. Nevertheless, this phenomenon can lead to product deposits that are too significant: The feel of the hair becomes laden, unpleasant; the hair becomes stiff and there is an inter-fibre adhesion which affects styling.

A new generation of products has recently been developed to overcome these disadvantages. It is based on comb structured (meth)acrylic copolymers. The use of these products for hair care was described in documents EP 1 632 508 A1 and EP 2 168 991 A1. It will be apparent that their use in a shampoo formulation allows not only an improvement in its styling effect, but also facilitates its elimination after rinsing with water.

The expression "(meth)acrylic comb copolymer" is intended to designate a copolymer consisting of a skeleton that is essentially linear and of a (meth)acrylic type on which are grafted at least 2 side segments consisting of at least one "macromonomer". The term "marcromonomer" refers to a water-soluble polymer or copolymer having at least one terminal group with an unsaturated ethylene function.

In the case of products developed for hair care and described in documents EP 1 632 508 A1 and EP 2 168 991 A1, this macromonomer is of the hydroxyl methacrylate or methoxy polyethylene glycol type (MPEG or MAMPEG methacrylate). In summary, the comb copolymers described in these two documents are the result of the synthesis between a first anionic monomer which can be (meth)acrylic acid, and an alkoxy or hydroxy polyakylene glycol macromonomer with the formula R—(EO)$_n$—R', with:

EO designating ethylene oxide and n being an integer between 3 and 300,

R designating an unsaturated polymerizable function such as the methacrylate function, R' representing hydrogen or a carbon radical with from 1 to 30 carbon atoms.

In these two documents will be noted all the importance given to the specific macromonomers MPEG550 and MPEG2000, methoxypolyethylene glycol methacrylate with a mean molar mass by weight equal to 550 g/mol and 2,000 g/mol respectively.

SUMMARY OF THE INVENTION

Now, quite surprisingly, the inventors have developed the use of (meth)acrylic comb copolymers with a different structure that have proven to be more efficient at the level of the hair styling effect and in terms of elimination by rinsing with water. These polymers comprise, consist essentially of, or consist of:

a) at least one monomer which is (meth)acrylic acid, and b) at least one macromonomer with the formula (I):

$$R\text{—}(PO)_m\text{-}(EO)_n\text{—}R' \qquad (I)$$

m and n are each non-zero integers less than 150,

PO and EO respectively designate propylene oxide and ethylene oxide,

R designates a polymerizable unsaturated function,

R' represents hydrogen or an alkyl group with from 1 to 4 carbon atoms.

In these polymers the monomers exist in polymerized form, but are nevertheless referred to as monomers in accord with convention.

These structures differ from those mentioned in documents EP 1 632 508 A1 and EP 2 168 991 A1 in at least the sense that their macromonomer contains both ethylene oxide and propylene oxide links. There was nothing to suggest that such a modification would impact in such a beneficial way the properties of styling effect and rinseability of the shampoos in which these polymers would be incorporated.

In addition, it is stated that the macromonomer of formula (I) is well known and described in patent U.S. Pat. No. 6,034, 208. Also, the manufacture of the copolymers as indicated above, which are manufactured from this macromonomer, is well known to the person skilled in the art, notably in a continuous, semi-continuous or batch process (see documents U.S. Pat. Nos. 6,815,513, 6,214,958, 6,664,360 and 7,232,875). Finally, other uses of these structures were already known: notably as additives in formulations of plaster (EP 1 377 533 A1, EP 1 615 860 A1), of cement (FR 2 939 128 A1 and FR 2 939 428 A1) or in paper coating dispersions (French application not yet published and filed under number FR 10 54575).

A first object of the present invention is the use as a styling agent in a cosmetic formulation of at least one (meth)acrylic comb copolymer. These comb copolymers comprise, consist essentially of, or consist of:
  a) at least one monomer which is (meth)acrylic acid, and
  b) at least one macromonomer of formula (I):

$$R\text{—}(PO)_m\text{-}(EO)_n\text{—}R' \quad (I)$$

m and n are each non-zero integers less than 150,
  PO and EO respectively designate propylene oxide and ethylene oxide,
  R designates a polymerizable unsaturated function,
  R' represents hydrogen or an alkyl group with from 1 to 4 carbon atoms.

This utilisation is also preferably characterized in that the (meth)acrylic comb copolymer comprises, consists essentially of, or consists of, expressed as a percentage by weight of each of its components:
  a) from 5% to 30%, preferentially from 15% to 25% of at least one monomer which is (meth)acrylic acid,
  b) from 70% to 95%, preferentially from 75% to 85% of at least one macromonomer with formula (I),
  c) from 0% to 20%, preferentially from 0% to 10% of at least one monomer which is an ester of (meth)acrylic acid, preferentially ethyl acrylate,
where preferably the sum of the percentages a), b), and c) are equal to 100%.

In a preferred embodiment, this utilisation is characterized in that R designates the methacrylate or methacrylurethane function.

In a preferred embodiment, this use is characterized in that R' designates hydrogen.

In a preferred embodiment, this use is characterized in that n and m are between 10 and 90. Structures —$(PO)_m$-$(EO)_n$— designate both block structures as well statistical structures, and this is true for the entire Application.

In a preferred embodiment the (meth)acrylic comb copolymer presents a mean molar mass by weight of between 20,000 g/mol and 6,000,000 g/mol, preferentially between 40,000 and 1,000,000 g/mol.

The (meth)acrylic comb copolymer can be obtained for example by free radical polymerization in solution, in direct or inverse emulsion, in suspension or precipitation in solvents, in the presence of catalytic systems and transfer agents, or even in a controlled radical polymerization and preferentially in polymerization controlled by a nitroxides (NMP) or by cobaloximes, in polymerization by atom transfer radical polymerization (ATRP), by controlled radical polymerization by sulphur derivatives, selected from among the carbamates, dithioesters or trithiocarbonates (RAFT) or the xanthates.

It may be fully or partially neutralized by one or more neutralizing agents with a monovalent or polyvalent cation, the said agents being preferentially being selected from ammonium hydroxide or among the hydroxides and/or oxides of calcium, magnesium, or among the hydroxides of sodium, potassium, lithium, or among the primary, secondary or tertiary aliphatic and/or cyclic amines such as preferentially stearylamine, ethanolamines (mono-, di-, triethanolamine), mono and diethylamine, cyclohexylamine, methylcyclohexylamine, amino methyl propanol, morpholine, and preferentially in that the neutralizing agent is chosen from among triethanolamine and sodium hydroxide.

It can also be separated into several phases according to static or dynamic processes by one or more polar solvents preferentially belonging to the group consisting of water, methanol, ethanol, propanol, isopropanol, the butanols, acetone, tetrahydrofuran or their mixtures.

This utilisation is also characterized in that the cosmetic formulation preferably comprises from 0.01% to 50%, more preferentially from 0.1% to 30%, very preferentially from 3% to 20% by dry weight of the said copolymer with respect to its total weight.

This utilisation is also preferably characterized in that the formulation includes at least one constituent chosen from among water, hydrophilic organic solvents and preferentially alcohols, preferentially monoalcohols, linear or branched in C1-C6 and polyols and glycol ethers, preferentially in C2, and aldehydes in C2-C4 hydrophylic, waxes, pasty fats, gums and their mixtures, of animal, vegetable, mineral or synthetic origin, lipophilic organic solvents, oils of animal, vegetable, mineral or synthetic origin, synthesis esters and ethers, pentaerythritol esters, the fatty alcohols with 12 to 26 carbon atoms, fluorinated oils, partially hydrocarbonated and/or siliconated, siliconated oils, volatile or not, linear or cyclical, liquid or pasty at room temperature, pigments, nacres, fillers, water-soluble dyes, fat-soluble dyes, filmification agents, surfactants, vitamins, perfumes, nacrating agents, thickeners, gelling agents, trace elements, softeners, retention aids, perfumes, alkalinizing or acidifying agents, preservatives, solar filters, anti-oxidants, the anti hair loss agents, anti-dandruff agents, propellant agents, ceramides and their mixtures.

This utilisation is also preferably characterized in that the formulation presents in the form of a capillary composition, preferentially for the maintenance of hair styling or the shaping of hair, very preferentially in the form of shampoos, gels, waving lotions, brushing lotions, of setting and styling compositions chosen from the lacquers or sprays, after-shampoos whether rinsed or not, compositions for permanents, straightening, dyeing or bleaching or again, in the form of compositions for rinsing, for application before or after a dyeing, a bleaching, a permanent or a straightening, or again between the two steps of a permanent or a straightening.

Another object of the present invention consists of a cosmetic formulation comprising at least one (meth)acrylic comb copolymer that comprises, consists essentially of, or consists of:
  a) at least one monomer which is (meth)acrylic acid, and
  b) at least one macromonomer with the formula (I):

$$R\text{—}(PO)_m\text{-}(EO)_n\text{—}R' \quad (I)$$

m and n are each non-zero integers less than 150,
  PO and EO respectively designate propylene oxide and ethylene oxide,
  R designates a polymerizable unsaturated function,
  R' represents hydrogen or an alkyl group with from 1 to 4 carbon atoms.

This formulation is also preferably characterized in that the (meth)acrylic comb copolymer comprises, consists essentially of, or consists of, expressed as a percentage by weight of each of its components:
  a) 5% to 30%, preferentially of 15% to 25% of at least one monomer which is (meth)acrylic acid,
  b) 70% to 95%, preferentially of 75% to 85% of at least one macromonomer with formula (I), c) 0% to 20%, preferentially of 0% to 10% of at least one monomer which is an ester of (meth)acrylic acid, preferentially ethyl acrylate, the sum of the percentages a), b), and c) preferably being equal to 100%.

In a preferred embodiment, this formulation is characterized in that for the said copolymer, R designates the methacrylate or methacrylurethane function.

In a preferred embodiment, this formulation is characterized in that for the said copolymer, R' designates hydrogen.

In a preferred embodiment, this formulation is characterized in that for the copolymer, n and m are between 10 and 90.

This formulation is also preferably characterized in that for the copolymer it presents a mean molar mass by weight of between 20,000 g/mol and 6,000,000 g/mol, preferentially between 40,000 g/mol and 1,000,000 g/mol.

This formulation is also preferably characterized in that the cosmetic formulation comprises from 0.01% to 50%, more preferentially from 0.1% to 30%, very preferentially from 3% to 20% by dry weight of the said copolymer with respect to its total weight.

This formulation is also preferably characterized in that it includes at least one constituent chosen from among water, hydrophilic organic solvents and preferentially alcohols, preferentially monoalcohols, linear or branched in C1-C6 and polyols and glycol ethers, preferentially in C2, and aldehydes in C2-C4 hydrophylic, waxes, pasty fats, gums and their mixtures, of animal, vegetable, mineral or synthetic origin, lipophilic organic solvents, oils of animal, vegetable, mineral or synthetic origin, synthesis esters and ethers, pentaerythritol esters, the fatty alcohols with 12 to 26 carbon atoms, fluorinated oils, partially hydrocarbonated and/or siliconated, siliconated oils, volatile or not, linear or cyclical, liquid or pasty at room temperature, pigments, nacres, fillers, water-soluble dyes, fat-soluble dyes, filmification agents, surfactants, vitamins, perfumes, nacrating agents, thickeners, gelling agents, trace elements, softeners, retention aids, perfumes, alkalinizing or acidifying agents, preservatives, solar filters, anti-oxidants, the anti hair loss agents, anti-dandruff agents, propellant agents, ceramides and their mixtures.

This formulation is also preferably characterized in that it presents in the form of a capillary composition, preferentially for the maintenance of hair styling or the shaping of hair, very preferentially in the form of shampoos, gels, waving lotions, brushing lotions, of setting and styling compositions chosen from the lacquers or sprays, after-shampoos whether rinsed or not, compositions for permanents, straightening, dyeing or bleaching or again, in the form of compositions for rinsing, for application before or after a dyeing, a bleaching, a permanent or a straightening, or again between the two steps of a permanent or a straightening.

Another object of the present invention is a cosmetic hair treatment process characterized in applying to the hair a cosmetic formulation as defined above. As used herein, hair includes human hair. Preferably the hair is wet prior to application.

The following examples will allow a better understanding of the invention, without however limiting its scope.

EXAMPLES

A shampoo composition is prepared that comprises the following components (in weight %):
   7.5% of lauryl ether sulphate,
   2.5% of coconut betaine amphoteric surfactant (Dehyton AB30 from Cognis™)
   5% of coconut polyglucoside surfactant (Plantacare 818 UP from Cognis™)
   3% (by dry weight) of the polymer to be tested,
   QS 100% water Test No. 1

This test demonstrates the prior art, and implements a copolymer consisting of, expressed in % by weight of each of its monomers:
   a) 20% methacrylic acid,
   b) 80% of a macromonomer with formula (I):

R—(PO)$_m$-(EO)$_n$—R'  (I)

m=0, n=48,
   PO and EO respectively designate propylene oxide and ethylene oxide,
   R designates the methacrylate function,
   R' represents the methyl radical.
totally neutralized by sodium hydroxide and with a mean molecular mass by weight equal to 25,000 g/mol.

Macromonomer (I) is thus here MPEG methacrylate with a mean molar mass equal to 2,000 g/mol (illustrated in documents EP 1 632 508 A1 and EP 2 168 991 A1).

Test No. 2

This test demonstrates the prior art, and implements a copolymer consisting of, expressed in % by weight of each of its monomers:
   a) 20% methacrylic acid,
   b) 80% of a macromonomer with formula (I):

R—(PO)$_m$-(EO)$_n$—R  (I)

m=0, n=110,
   PO and EO respectively designate propylene oxide and ethylene oxide,
   R designates the methacrylate function,
   R' represents the methyl radical,
totally neutralized by sodium hydroxide and with a mean molecular mass by weight equal to 60,000 g/mol.

Macromonomer (I) is thus here MPEG methacrylate with a mean molar mass by weight equal to 5,000 g/mol.

Test No. 3

This test demonstrates the invention, and implements a copolymer consisting of, expressed in % by weight of each of its monomers:
   a) 20% methacrylic acid,
   b) 80% of a macromonomer with formula (I):

R—(PO)$_m$-(EO)$_n$—R'  (I)

m=15, n=46,
   PO and EO respectively designate propylene oxide and ethylene oxide,
   R designates the methacrylate function,
   R' represents the hydroxy radical,
totally neutralized by sodium hydroxide and with a mean molecular mass by weight equal to 60,000 g/mol.

In humid and thy environments, good untangling properties and an improved styling in the case of the polymer No. 3 according to the invention are observed. It is also apparent there is a more pronounced capacity of this polymer to be eliminated by rinsing the hair in water.

The above written description of the invention provides a manner and process of making and using it such that any person skilled in this art is enabled to make and use the same, this enablement being provided in particular for the subject matter of the appended claims, which make up a part of the original description.

As used herein, the words "a" and "an" and the like carry the meaning of "one or more." The phrases "selected from the group consisting of," "chosen from," and the like include mixtures of the specified materials. Terms such as "contain(s)" and the like are open terms meaning 'including at least' unless otherwise specifically noted.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A cosmetic formulation for treating hair comprising a (meth)acrylic comb copolymer, said comb copolymer comprising:
    a) at least one (meth)acrylic acid monomer; and
    b) at least two macromonomers of formula (I):

$$R—(OCH_2—CH(CH_3))_m(OCH_2CH_2)_n—R' \qquad (I)$$

wherein variables m and n are integers between 10 and 90;
   wherein $—(OCH_2—CH(CH_3))_m(OCH_2CH_2)_n—$ include block and statistical structures;
   wherein R designates a polymerizable unsaturated function;
   wherein R' is a hydrogen atom, or an alkyl group having from 1 to 4 carbon atoms;
   wherein at least two side chains of the comb copolymer comprise the $—(OCH_2—CH(CH_3))_m(OCH_2CH_2)_n—R'$ segment of formula (I);
   wherein the (meth)acrylic acid monomers are 5% to 30% by weight of the comb polymer; and
   wherein the macromonomers of formula (I) are 70% to 95% by weight of the comb copolymer.

2. The cosmetic formulation according to claim 1, wherein the (meth)acrylic comb copolymer comprises, expressed as a percentage by weight of each of its components:
    a) 15% to 25% of (meth)acrylic acid,
    b) 75% to 85% of a macromonomer with formula (I), and
    c) 0% to 20% of a monomer which is an ester of (meth)acrylic acid,
   the sum of the percentages a), b), and c) being equal to 100%.

3. The cosmetic formulation according to claim 1, wherein R' is a hydrogen atom.

4. The cosmetic formulation according to claim 1, wherein the copolymer has a mean molar mass by weight of 20,000 g/mol-6,000,000 g/mol.

5. The cosmetic formulation according to claim 1, wherein the cosmetic formulation comprises from 0.01% to 50% of said copolymer with respect to its total weight.

6. The cosmetic formulation according to claim 5, wherein the cosmetic formulation comprises from 3% to 20% of said copolymer with respect to its total weight.

7. The cosmetic formulation according to claim 1, wherein the cosmetic formulation further comprises at least one constituent chosen from water, monoalcohols, linear or branched in C1-C6 and polyols, glycol ethers, waxes, pasty fats, gums, oils of animal, vegetable, mineral or synthetic origin, pentaerythritol esters, fatty alcohols with 12 to 26 carbon atoms, fluorinated oils, partially hydrocarbonated and/or siliconated, siliconated oils, pigments, nacres, fillers, water-soluble dyes, fat-soluble dyes, filmification agents, surfactants, vitamins, perfumes, nacrating agents, thickeners, gelling agents, trace elements, softeners, retention aids, perfumes, alkalinizing agents, acidifying agents, preservatives, solar filters, antioxidants, anti hair loss agents, anti-dandruff agents, propellant agents, ceramides, and mixtures thereof.

8. The cosmetic formulation according to claim 1, wherein the cosmetic formulation is a shampoo, gel, waving lotion, brushing lotion, setting and styling composition chosen from lacquers and sprays, after-shampoo whether rinsed or not, or is a composition for permanents, straightening, dyeing or bleaching.

9. The cosmetic formulation according to claim 1, wherein the cosmetic formulation is a composition for rinsing or for application before or after a dyeing.

10. A method, comprising applying the cosmetic formulation according to claim 1 to hair.

11. The method of claim 10, comprising applying the cosmetic formulation to wet hair.

12. The cosmetic formulation according to claim 1, wherein R is a methacrylate function.

13. The cosmetic formulation according to claim 1, wherein R is a methacrylurethane function.

* * * * *